United States Patent
Hustert

(10) Patent No.: US 6,583,878 B2
(45) Date of Patent: Jun. 24, 2003

(54) PROCESS AND APPARATUS FOR MEASURING OPTICAL PARAMETERS ON LIQUID MEDIA

(75) Inventor: Hans-Hendrik Hustert, Dortmund (DE)

(73) Assignee: E. I. du Pont de Nemours and Company, Wilmington, DE (US)

( * ) Notice: Subject to any disclaimer, the term of this patent is extended or adjusted under 35 U.S.C. 154(b) by 126 days.

(21) Appl. No.: 09/734,136

(22) Filed: Dec. 11, 2000

(65) Prior Publication Data

US 2001/0043329 A1 Nov. 22, 2001

(30) Foreign Application Priority Data

Dec. 17, 1999 (DE) .......................................... 199 60 919

(51) Int. Cl.⁷ .................................................. G01J 3/50
(52) U.S. Cl. ....................................... 356/402; 356/244
(58) Field of Search ................................ 356/402, 410, 356/440, 244, 409, 425, 51, 444; 73/53.01; 250/576, 226

(56) References Cited

U.S. PATENT DOCUMENTS

| | | | | |
|---|---|---|---|---|
| 4,204,766 A | * | 5/1980 | Harada ........................ | 356/244 |
| 4,236,486 A | * | 12/1980 | Nakamine et al. .......... | 356/246 |
| 4,936,685 A | * | 6/1990 | Taylor et al. ................. | 399/57 |
| 6,091,914 A | * | 7/2000 | Yoo ............................. | 399/57 |

FOREIGN PATENT DOCUMENTS

| DE | 25 25 701 | 12/1976 |
|---|---|---|
| DE | 25 31 459 | 2/1977 |

* cited by examiner

Primary Examiner—F. L. Evans
Assistant Examiner—Kara Geisel
(74) Attorney, Agent, or Firm—Bart E. Lerman

(57) ABSTRACT

Process and apparatus for measuring optical, especially calorimetric, parameters on liquid, colored media, especially on wet lacquers, in which the liquid, colored medium is applied to a continuously moving, cylindrical support, a film of the liquid, colored medium forms on the continuously moving, cylindrical support, and optical, especially calorimetric, parameters are measured on the film of the liquid, colored medium.

10 Claims, 2 Drawing Sheets

PROCESS AND APPARATUS FOR MEASURING OPTICAL PARAMETERS ON LIQUID MEDIA

BACKGROUND OF THE INVENTION

The invention relates to a process for measuring optical, especially colorimetric, parameters on liquid, coloured media, especially on wet lacquers, and to an apparatus for carrying out the process.

In the lacquers industry it is necessary in the various production, standardisation and development stages of lacquer manufacture and lacquer development to carry out optical measurements on the lacquers for the purposes of quality control. In that manner, information is obtained as to whether the lacquers meet the required optical parameters, for example the required colour strength, and any corrective steps that are required can be taken. Measurement may in principle be carried out on wet lacquers or on applied and dried, or hardened, lacquers. In the standardisation of lacquers, for example in the manufacture of standardised mixed lacquers or pigment pastes for automotive repair, measurement on applied and hardened lacquers, for example on coated metal sheets, is essential because that method, in comparison with measurement on wet lacquers, is concerned with the appearance of the film of lacquer finished by drying or hardening, and ultimately it is the perceived colour of the applied lacquer which is important and not that of the wet lacquer.

However, measurement on applied lacquers is relatively complicated because, before measurement can be carried out, coated metal sheets, so-called test or sample plates, must first be produced. To that end, for example in the case of plain colours, a mixture of each colour with white lacquer must first be prepared and then applied and dried or hardened. In the standardisation of pigment pastes, there is the additional step of lacquering-up with appropriate binders before the application.

In particular applications, however, such as, for example, in the first test steps in the standardisation or manufacture of lacquers, and also for delivery monitoring, it is sufficient, in order to determine intermediate results, to carry out the calorimetric measurements initially on the wet lacquer, which can be effected substantially more rapidly and less expensively than measurements on the applied hardened lacquer. Colour-measuring devices that can be used are known and commercially available. Corresponding measuring cells for wet-lacquer measurement are likewise known. Such cells are, for example, cylindrical or cuboidal glass measuring vessels, which are placed in front of the measuring aperture of the colour-measuring device. A disadvantage of such simple measuring cells is that the accuracy of the measuring results obtained therewith is unsatisfactory, for example caused by rapid deposition of the lacquer in the vessel or by the influence of the intermediate medium glass, for example owing to physical interactions.

Furthermore, a method of colorimetry on liquid lacquers is described in DE-A-2531459, in which method the lacquer is removed from the mixing container by means of an overflow vessel, which is arranged in a raisable manner in a mixing container containing lacquer, and fresh lacquer from the mixing container is introduced into the lacquer in the overflow vessel by way of a pipe, and the surface of the lacquer in the overflow vessel is measured by colorimetry.

DE-A-2525701 describes a further method of colorimetry on liquid lacquers. In that method, a continuous thin film is formed from the lacquer to be tested, and a portion of the film is measured by colorimetry. In that method, the film of lacquer may be a film that moves with a support or a film that moves with a laminar flow over a support. In the first case, the support is a measuring disk that is rotatable about a horizontal axis, and in the second case it is a plate-like body having an approximately vertical surface. In both cases, the lacquer is applied to the respective support by means of a pouring tank having an outlet opening. A disadvantage of that method in the case of the use of a rotatable measuring disk is that a disk of an acceptable size can only be used when colour-measuring devices having a measuring aperture arranged more to the side of the housing are employed. With colour-measuring devices having measuring apertures arranged centrally, extremely large disks must be used. In the case of the use of a vertical plate-like body, flocculation effects may occur owing to the absence of shear. The effect of gravity and the disadvantages associated therewith must also be taken into account. For example, it is only possible to work with layer thicknesses of the wet lacquer that are above the run-off limit.

Accordingly, the object of the invention was to provide a process for measuring optical, especially colorimetric, parameters on liquid, coloured media, especially on wet lacquers, which process permits rapid and effective measurement of the optical parameters and at the same time ensures the accuracy of measurement required, for example, for quality control purposes. The process is to be such that measuring devices having any desired arrangement of the measuring aperture can be used in the optimum manner.

SUMMARY OF THE INVENTION

The object is achieved by a process for measuring optical, especially calorimetric, parameters on liquid, coloured media, especially on wet lacquers, which process is characterised in that the liquid, coloured medium is applied to a continuously moving cylindrical support, a film of the liquid, coloured medium forms on the continuously moving cylindrical support, and optical, especially calorimetric, parameters are measured on the film of the liquid, coloured medium.

Optical parameters to be measured are, for example, brightness and calorimetric parameters, such as colour strength or colour difference.

The liquid, coloured media are especially liquid lacquers. Accordingly, for the purposes of simplicity, the term lacquer will always be used hereinbelow, but that term is to be understood as including in principle also other liquid media.

Application of the lacquer to the cylindrical support, hereinafter called the roller for short, may be effected by various methods, for example by pouring, spraying, roller application, knife application or brush application. It is preferably carried out by pouring or knife application. That may be effected by means of a suitable device, for example by means of a vessel or a box knife.

When the lacquer has been applied to the roller, the measurement may be carried out. In order to protect the measuring device from contamination by the lacquer, the roller is preferably not positioned directly in front of the measuring aperture of a corresponding measuring device until shortly before the measurement. However, it is also possible to connect the roller and the measuring device together at the required distance for the measurement and to apply the lacquer in that position.

The process according to the invention will be described in greater detail below.

DETAILED DESCRIPTION OF THE INVENTION

In a first process step, the lacquer is applied by a suitable method to the roller, which is already rotating. The roller is preferably arranged horizontally or vertically with respect to the measuring aperture of the measuring device. A horizontal arrangement may be used, for example, in the case of very high viscosity lacquer materials. In general, however, a vertical arrangement is preferred. The roller is made to rotate by a set of gears which can be driven by a drive device.

The roller to be used in the process according to the invention as the support for the lacquer may be in various forms. For example, the roller may be a hollow cylinder of variable wall thickness, or a solid cylinder, it being possible for a solid cylinder to be hollowed out on the inside for weight reasons. The roller is preferably made of metal, especially of high-grade steel. The dimensions of the roller may be varied within certain limits. The width of the roller cylinder is dependent, for example, on the type and size of the measuring device, especially colour-measuring device and measuring aperture. The roller with the applied film of lacquer is positioned in front of the measuring aperture of the corresponding measuring device. The width of the film of lacquer is to cover the measuring aperture and, preferably, also the area surrounding the measuring aperture. The width of the film of lacquer is itself determined, for example, by the size and construction of the device with which the lacquer can be applied to the roller. Further details are given below regarding the form of the device preferably to be employed therefor. The width of the roller is to be such that areas of the roller that are free of lacquer film remain on both sides of the film of lacquer formed on the roller. For example, approximately from 5 to 30%, based on the width of the film of wet lacquer, of uncovered roller surface are to remain on each side. The diameter of the roller is preferably to be so chosen that the curvature of the cylinder, based on the size of the measurement area, can be disregarded, so that it is possible to start from a flat surface within the measurement area.

The size of the measurement area covered by the measuring device may be different with different measuring devices, especially with colour-measuring devices, and is dependent, for example, on whether plain lacquers (lacquers pigmented with absorption pigments) or special-effect lacquers (lacquers pigmented with plate-like metal-effect pigments) are to be measured. For example, in the measurement of plain lacquers it is possible to start from a flat surface within the measurement area with a roller diameter of, for example, greater than/equal to 15 cm, preferably greater than/equal to 20 cm. The upper limit of the roller diameter is determined, for example, by the fact that excessively large evaporation areas, based on the applied film of wet lacquer, must not be formed. Preferably, the roller diameter may be from 18 to 30 cm.

Application of the lacquer to the rotating roller may be carried out as already mentioned above, preferably by means of a suitable device for holding the lacquer to be measured, especially a container in the form of a vessel. The container may be arranged at any desired location on the periphery of the roller. It may be located, for example, on the same side of the roller as the measuring device, that is to say in the immediate vicinity of the measuring device, but it may also be located further away from the measuring device, for example on the opposite side of the roller. The container is preferably located on the opposite side of the roller, so that the measuring device and the container are located substantially at a distance from one another that corresponds approximately to the diameter of the roller. By means of the last-mentioned arrangement, any contamination of the colour-measuring device, and especially of the measuring aperture, caused by the application of the lacquer can be avoided.

A preferred container suitable for application of the lacquer has an inlet opening for the lacquer and an outlet opening through which the lacquer is able to reach the roller. The outlet opening is preferably a slot-like outlet opening. The container may be, for example, a vessel which is preferably approximately cube-shaped or cuboidal in construction. The vessel may be open or closed at the top. However, the vessel must have a suitable inlet opening for introduction of the lacquer material. Accordingly, there is preferably used a cube-shaped or cuboidal vessel that is open at the top and has a slot-like outlet opening.

In the following description of the process according to the invention, reference will be made especially to the preferred embodiment having a roller arranged vertically in front of the measuring aperture of the colour-measuring device, and having a vessel as the application device.

In order that the lacquer can reach the roller, the vessel is first brought up close to the roller. In order to be able to bring the vessel up to the roller with an accurate fit and bring it into contact therewith, one of the vertical boundary surfaces of the vessel is preferably curved to match the curvature of the roller. The slot-like opening through which the lacquer material can pass from the vessel onto the roller is preferably located at the edge between the base surface and the curved boundary surface of the vessel. The slot-like opening extends over the entire inside width of the vessel. However, the slot-like opening does not extend over the walls of the vessel. The slot-like opening has the same slot width over its entire longitudinal extent. The vessel is preferably in such a form that it is completely open on its side facing the roller. In that case, the side walls facing the roller are curved on their narrow side to match the curvature of the roller, and rest against the roller.

The slot-like opening in the vessel may be produced, for example, by the base of the vessel being at a suitable distance from the roller. In that preferred case of a vessel that is open on its side facing the roller, the outlet slot is limited by the roller and the base of the vessel.

In the above-mentioned case, the vessel is brought up to the roller and brought into contact therewith in such a manner that the curved narrow sides of the side walls rest flush against the roller. The vessel may be held in the desired position preferably by means of a holding device and/or by means of suitable positioning elements, for example spring elements.

Since the lacquer material passes onto the roller through the slot-like opening in the base region of the vessel, the length of the slot corresponds to the width of the film of wet lacquer formed on the roller, and the width of the slot corresponds to the layer thickness of the wet film that is applied. The width of the slot is such that the required layer thickness results therefrom.

It will be seen from the above that the size of the roller and the size of the vessel are advantageously matched to one another. The width of the vessel is preferably to be approximately from 40 to 90%, especially from 50 to 80%, of the width of the roller cylinder.

The vessel may be manufactured from various materials, for example from plastics or from metal. Suitable plastics are, for example, polypropylene, polyethylene, polycarbonate, polyethylene terephthalate or polyamide, individually or in admixture. Examples of suitable metals are aluminium, copper and zinc, or alternatively metal alloys such as copper or aluminium alloys, for example brass. However, the vessel is preferably made of plastics. The base of the plastics vessel may particularly preferably consist of metal or a metal alloy, for example those mentioned above. The base may preferably be of copper or brass. When a base of metal or a metal alloy is used, it is possible to adjust the edges of the slot-like opening of the vessel, and hence the layer thickness of the film of wet lacquer, particularly accurately.

The roller is made to rotate by means of a motor. The speed of rotation of the roller is also dependent on the chosen roller diameter. The speed of rotation may be, for example, from 40 to 120 rpm. Speeds of rotation of from 60 to 80 rpm have proved especially suitable in the case of roller diameters of, for example, from 18 to 25 cm. Where the roller is arranged vertically in front of the measuring aperture, the direction of rotation is preferably so chosen that the lacquer is able to reach the roller by gravity.

Only when the vessel has been brought up to the rotating roller in the appropriate manner can the lacquer material be introduced into the vessel. The lacquer material immediately flows through the slot-like opening in the base of the vessel onto the rotating roller and is distributed over the surface of the roller by the rotational movement. An unbroken film forms over the entire circumference of the roller, the width of which film corresponds to the length of the slot-like opening.

The roller continues to rotate until a uniform, bubble-free film has formed on the surface of the roller. It has proved advantageous to continue to rotate the roller for, for example, from 0.5 to 3 minutes. The layer thickness of the film of wet lacquer applied to the rotating roller is adjusted by way of the width of the slot-like opening in the vessel, or by the distance between the vessel and the roller. Layer thicknesses of, for example, from 0.2 to 4.0 mm can be set. Layer thicknesses of, for example, from 0.3 to 2.0 mm, preferably from 0.5 to 1.0 mm, have proved advantageous.

As soon as a uniform, bubble-free film has formed on the surface of the roller, the roller, or preferably the entire unit consisting of the vessel and the roller with the film of wet lacquer formed on the roller, is brought, optionally after a short resting phase, up to the measuring aperture of the measuring device, especially of the colour-measuring device, for example by means of a suitable movably mounted device, and the measurement is carried out; of course, the measuring device may also be brought up to the roller. The distance to the measuring aperture of the measuring device can preferably be adjusted by means of suitable stop elements. It has proved advantageous to adjust the distance so that it is approximately from 1 to 4 mm larger than the slot width or the layer thickness of the film of wet lacquer. The optical measurement may be carried out with the roller stationary or moving. The measurement is preferably carried out on the rotating roller in order to avoid unnecessary contamination by drops of lacquer.

Conventional measuring devices for determining optical parameters, such as are commercially available and known to the person skilled in the art, may be used as measuring devices. Conventional measuring devices suitable for the determination of remission curves may be used as colour-measuring devices. Examples of colour-measuring devices which may be used are the SF 600+(Datacolor International) and the X-Rite MA 58 (X-Rite). Colorimetric parameters for evaluation are, for example, colour strength and/or colour difference. The evaluation may be computer-assisted. The parameters determined are compared with the corresponding values of a model, for example of a release sample. To that end, the corresponding parameters of the model are measured in an analogous manner to those of the lacquer sample to be measured, and compared, it likewise being possible for the evaluation to be computer-assisted. Further details need not be given here regarding calorimetric measurements. They are known to the person skilled in the art. The foundations and principles of colorimetry and also colour-measuring devices suitable therefor are described, for example, in Römpp Lexikon Lacke und Druckfarben, Georg Thieme Verlag 1998, p. 220, 221, 223 and in Hans G. Völz, Industrielle Farbprüfung, VCH Verlagsgesellschaft mbH 1990.

After the measurement, the roller or, in the preferred case, the unit consisting of the roller and the vessel, is advantageously moved away from the measuring device again, or vice versa, and cleaning may be carried out. It is advantageous to continue rotating the roller even during the cleaning operation in order to avoid contamination by drops of lacquer. Cleaning of the roller may be carried out, for example, by stripping off the film of lacquer using a suction device provided with a stripping edge, in conjunction with solvents. Cleaning of the vessel may be effected, for example, by sucking out the lacquer material using a vacuum pump and cleaning further by means of ultrasound. In order to catch any lacquer spray or drops of lacquer occurring during the entire process, it is advantageous to use a drip device, for example a drip tray, arranged beneath the roller and the vessel.

The invention relates also to an apparatus for carrying out the process according to the invention, which apparatus can be used as a measuring head for corresponding measuring devices, especially colour-measuring devices. Accordingly, the invention relates also to an apparatus by means of which optical, especially calorimetric, parameters can be measured on liquid, coloured media, especially on wet lacquers. The apparatus is characterised by a driveable cylindrical support, on which a film of a coloured, liquid medium can be formed, a container for holding the coloured, liquid medium to be measured, by means of which the coloured, liquid medium can be applied to the driveable, cylindrical support, a drive device and a set of gears for the continuous movement of the cylindrical support, and, optionally, connecting elements which connect the cylindrical support, the container and the other components of the apparatus with one another.

The driveable cylindrical support and the container by means of which the coloured, liquid medium to be measured can be applied to the driveable cylindrical support have the preferred structural features already described above in the description of the process according to the invention. In the following description of the apparatus, the term roller will be used for the cylindrical support and the term lacquer will be used for the coloured liquid medium. The roller is preferably so disposed within the apparatus according to the invention that a vertical arrangement of the roller in front of the measuring device is obtained.

According to a preferred embodiment of the apparatus according to the invention, the container is located in a holding device which is connected to a carrier plate on which the motor, the set of gears and the roller are arranged. The holding device has positioning elements by means of which the container can be positioned in direct contact with the roller. Spring elements, for example, may be used as the positioning elements, which spring elements press the container against the roller with a slight pressure. However, the pressure must only be so great that the rotational movement of the roller is not braked thereby. The motor/set of gears/roller unit is preferably arranged on a movable carrier plate by means of which the entire measuring head can be brought up to the measuring device. The movable carrier plate, for example a metal plate, may be mounted, for example, on rails or rolls.

Figure 1:
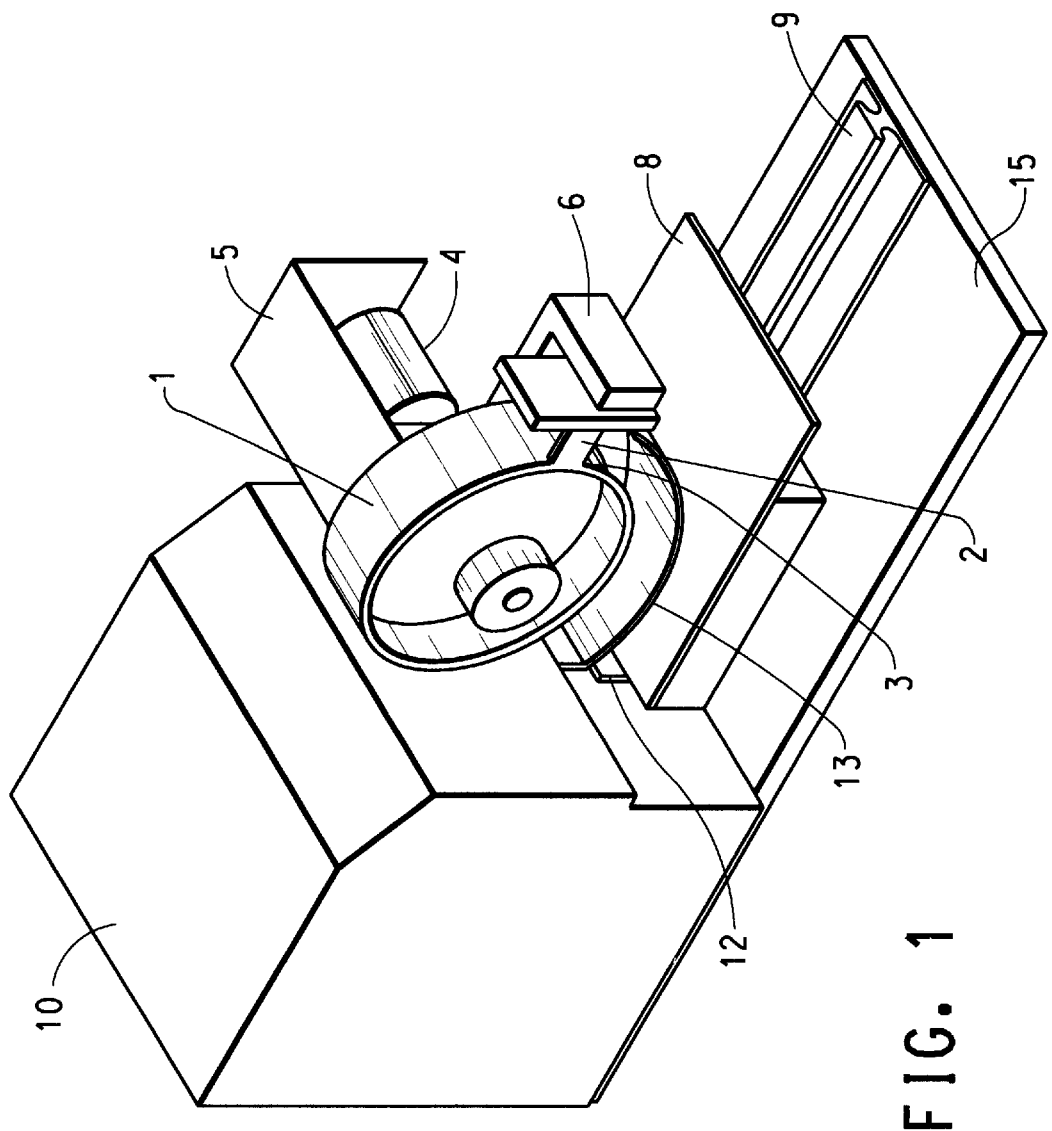
FIG. 1 shows an embodiment of the apparatus according to the invention.
Figure 2:
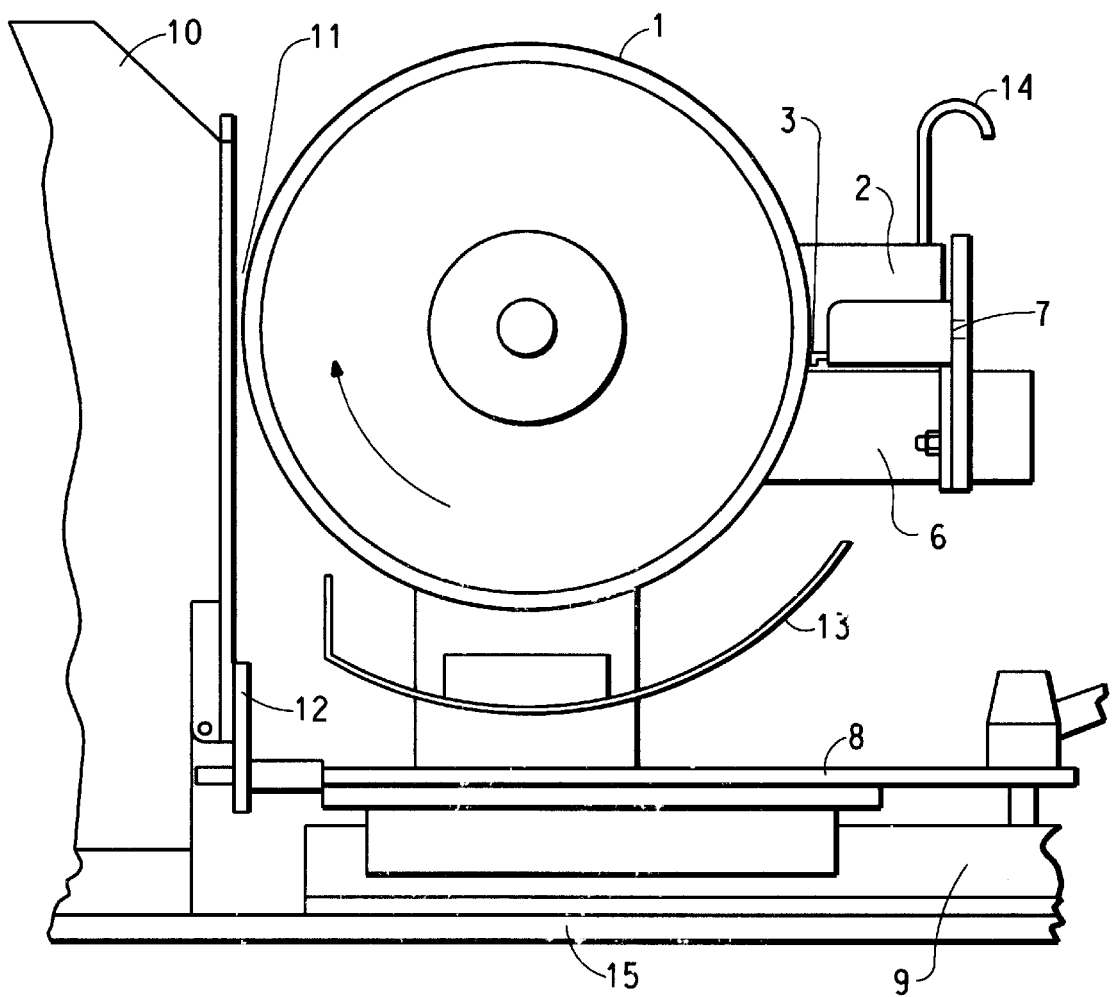
FIG. 2 shows a side view of an embodiment of the apparatus according to the invention.

In the Figures, 1 denotes a driveable roller consisting of a hollowed-out solid cylinder having a cylinder core, 2 denotes a vessel for holding the lacquer to be measured, having a slot-like opening 3 through which the lacquer is able to reach the driveable roller 1, and 4 denotes a motor/gears unit having a housing 5. The vessel 2 is positioned in a holder 6 against the roller 1 by means of spring elements 7. The holder 6 is connected to a carrier plate 8. The roller 1, the vessel 2, the holder 6 and the motor/gears unit 4 are arranged on the carrier plate 8. The carrier plate 8 can be moved by way of rail elements 9 and positioned in front of the measuring device 10 having the measuring aperture 11. The rail elements 9 are connected to the measuring device 10 by way of the releasable connection 12. Beneath the roller 1 there is arranged on the carrier plate 8 a drip tray 13 for catching drops of lacquer. For the purposes of better handling, the vessel 2 has a handle 14. The colour-measuring device 10, the entire measuring head on the carrier plate 8, and the rail elements 9 are removably arranged on a base plate 15.

The process according to the invention for measuring optical parameters on, especially, wet lacquers is not subject to any limitations as regards the nature of the lacquers. It can be used for measuring optical, especially calorimetric, parameters on any types of lacquer. The lacquers may be, for example, colour-giving lacquers pigmented with absorption pigments, so-called plain lacquers, metal-effect lacquers pigmented with metal pigments, for example aluminium pigments, and, optionally, other pigments, or special-effect lacquers pigmented with interference pigments or any other special-effect pigments. The lacquers may contain any desired types of pigment in combination with one another. The measurements may be carried out both on solvent-based and on water-based lacquers. The further composition of the lacquers, for example in respect of binders, additives and other lacquer constituents, is not important. The lacquers must simply be such that they can be applied without difficulty to the cylindrical support, and the formation of a homogeneous film is ensured.

The process according to the invention for wet-lacquer measurement allows calorimetric measurements to be carried out on wet lacquers rapidly and effectively and with the required accuracy of measurement, irrespective of the colour-measuring device used, in particular irrespective of the arrangement of the measuring aperture on the colour-measuring device.

The process according to the invention may be used in the lacquers industry both in the case of quality assurance in lacquer manufacture and lacquer standardisation, and in the various development stages of lacquer development. In particular, it is used in the evaluation of intermediate results in colouring processes in lacquer manufacture and lacquer standardisation, for example in the production of standardised mixed lacquers or standardised pigment pastes. In such processes, intermediate values are determined which are still relatively far removed from the end result, and it is therefore to be possible to determine them rapidly and effectively but with the required accuracy.

The process according to the invention may also be used, for example, in the field of printing inks. Of course, the process according to the invention and the apparatus for carrying out the process may in principle be used also in any other fields of application in which, in general, optical and, especially, colorimetric measurements on coloured, liquid media are required.

What is claimed is:

1. A process for measuring the optical parameters of a colored liquid lacquer which comprises the following steps:

1) applying the colored liquid lacquer from a container having a base with a slot like opening continuously to a rotating cylindrical support whereby a thin uniform film of the colored lacquer is formed on the cylindrical support;

2) rotating the film on the cylindrical support before a conventional optical measuring device whereby the optical measuring device measures the optical properties of the colored liquid lacquer, wherein the optical properties measured are brightness or colorimetric parameters or both.

2. The process according to claim 1 wherein the colorimetric parameters measured are color strength or color difference or both.

3. The process according to claim 1 wherein the rotating cylindrical support is positioned on a stationary platform.

4. The process according to claim 1 wherein the rotating cylindrical support is positioned on a movable platform.

5. The process according to claim 1 wherein the rotating cylindrical support is arranged horizontally in front of the optical measuring device.

6. The process according to claim 1 wherein the rotating cylindrical support is arranged vertically in front of the optical measuring device.

7. The process according to claim 1 which comprises forming a uniform bubble free film on the cylindrical support and moving the cylindrical support into close relationship with the optical measuring device wherein said measuring device has an or measuring optical properties.

8. An apparatus for measuring the optical parameters of a colored liquid lacquer, comprising:

a rotatable cylindrical support;

a container for holding colored liquid lacquer and having a slot-like opening wherein the colored liquid lacquer is applied as a film to the rotatable cylindrical support;

a drive device connected to the rotatable cylindrical support that continuously rotates the cylindrical support;

an optical device for measuring brightness or colorimetric parameters or both; and optionally, elements for connecting the cylindrical support and the container.

9. The apparatus according to claim 8 having a carrier plate, a holder connected to the carrier plate, and wherein the container is located in the holder, and the drive device comprises a motor mounted on the carrier plate, and wherein the holder has positioning elements whereby the container can be positioned in direct contact with the cylindrical support.

10. The apparatus according to claim 8 wherein the apparatus has rails or rollers and the carrier plate is movably position on said rails or rollers.

* * * * *